United States Patent [19]

Frauenhoffer

[11] Patent Number: 4,466,539

[45] Date of Patent: Aug. 21, 1984

[54] SURGICAL BLADE REMOVER

[76] Inventor: Christopher M. Frauenhoffer, 950 Walnut St., Philadelphia, Pa. 19107

[21] Appl. No.: 502,448

[22] Filed: Jun. 9, 1983

[51] Int. Cl.³ .................. B65D 25/00; B65F 7/00; A61B 19/02; A61F 13/00
[52] U.S. Cl. .................................. 206/370; 206/359; 29/239
[58] Field of Search ................... 206/370, 63.5, 359

[56] References Cited

U.S. PATENT DOCUMENTS

| | | | |
|---|---|---|---|
| 619,188 | 2/1899 | Kirkwood | 206/63.5 |
| 4,168,777 | 9/1979 | Gaskell et al. | 206/370 |
| 4,318,473 | 3/1982 | Sandel | 206/370 |
| 4,395,807 | 8/1983 | Eldridge, Jr. et al. | 206/359 |

Primary Examiner—William T. Dixson, Jr.
Attorney, Agent, or Firm—John J. Simkanich

[57] ABSTRACT

A surgical blade remover for separating a surgical or scalpel blade from a handle or holder includes a single "vee" shaped slot or notch in a vertical standing plate for engaging the rear portion of the surgical blade upon the downward movement into the vee slot of the blade and the tang portion of the blade holder holding the blade, thereby wedging a portion of the blade against the sides of the vee forming the blade to be lifted off of the tang and ejected therefrom as the tang is moved further downwardly and withdrawn rearwardly out of the vee slot in a horizontal motion.

12 Claims, 7 Drawing Figures

SURGICAL BLADE REMOVER

BACKGROUND OF THE INVENTION

This invention relates to surgical knife or scalpel blade extractors and removers, and particularly relate to that type of extractor which will enable the doctor to free the blade from the tang of a blade holder with a one-handed operation.

The blade removing tool of Grieshaber, U.S. Pat. No. 3,172,316 includes a handle having a pocket at one end with a pair of parallel extending flange prongs. Each prong has a raised lip. A scalpel blade holder holds the blade on the tang end of a handle.

The handle must be held by one hand while the blade removing tool is held in the other hand. The blade is inserted into the pocket and freed by an upward motion of the tool with respect to the blade much like the operation of reverse direction nail pulling prongs.

The Grieshaber tool requires concentration in inserting the blade into the narrow pocket and for springing the blade free of the tang of the blade holder. The removal operation can present a possible hazard if sufficient care is not taken to assure that the blade is safely handled once free of the tang. Moreover, as it is the upturned lip on each of the flat prongs which provides the ejection force on the rear or heel of a blade, the blade must be considerably inserted into the pocket. Any contamination on the blade comes into considerable contact with the blade removing tool, and repeated use of such tool without sterilization provides considerable surface area for contaminating the tang and even the handle portion of the blade holder from repeated use of the blade removing tool and thereby carrying contamination to new blades.

Montelius, U.S. Pat. No. 3,373,491, shows a surgical knife of a design suitable for use only with slot type blade holders. The expelling tool has a toe portion which engages a receiving slot in the handle for ejecting the blade. This structure requires a two handed operation as both the ejecting tool and the blade holder must be manipulated at the same time. Also, the ejecting tool comes in intimate contact with both the blade and the blade holder and in repeated use can pass on contamination.

Brimmer, U.S. Pat. No. 4,106,620 discloses a combination surgical blade dispenser and surgical blade remover. The surgical blade is of a more typical design and mounts on the tang of a blade holder. This blade is removed from the tang by inserting the blade and tang into an enclosure which has a blade removing foot having a pair of rectangular projecting ears. The rear edge of the blade must pass over the ears during a rearward movement of the blade holder to be inserted between the rear edge of the blade and the tang.

Once the rectantular ears are wedged between the rear of the blade and the tang the handle may be rotated to pry the end of the blade free from the tang and then pulled out of the enclosure leaving the blade behind.

While this removal structure allows for one hand operation, it does require a considerable degree of manipulation to be certain that the ears properly wedge under the blade sufficiently to pry the blade from the tang. This manipulation, of necessity, must be time consuming.

Gaskall et al. U.S. Pat. No. 4,168,777 shows a scalpel blade remover and collector having a container with a sloping bottom and a rectangular aperture having a shoulder section. A blade holder, with the blade mounted onto the tang portion, is inserted through the aperture and then downwardly so that the tang rests upon the lower wall of the aperture. This springs the rear or heel of the blade upwardly as the shoulders displace that portion of the blade. The blade holder is removed rearwardly so that the upwardly displaced heel of the blade catches against a downwardly projecting lip which extends beyond the face of the container. This stops the movement of the blade and allows it to be deposited within the container once the blade holder is pulled free.

Magney, U.S. Pat. No. 4,180,162, shows a combination dispenser and disposal cartridge for a surgical blade. This cartridge includes a rectangular box having a rectangular aperture at one end. Removal of a used blade is accomplished inserting the blade carried by the tang blade holder through the aperture in the end of the wall until the tip of the blade is engaged between a downwardly projecting box and a rounded internal wall corner. This is a precise location which must be searched for in order to wedge the point of the blade to a precise location. The handle is then withdrawn rearwardly so that a projecting wedge member comes to wedge between the heel of the blade and the tang of the blade holder whereby the rear edge of the blade is stripped off of the tang by abutting against a shoulder keeping the blade within the box as the blade holder tang is removed through the aperture.

This operation requires precise placement of the blade and blade holder tang within the disposal cartridge and a precise placement to pry the blade free from the tang portion of the blade holder. A trial and error procedure would have to be practiced until the ejection of the blade from the tang is complete.

Thompson, U.S. Pat. No. 4,270,416, shows a scalpel blade extractor tool which is intended to be hand-held while the scalpel blade and blade holder is manipulated within the extractor. A tang carrying a scalpel blade including part of the handle connected to the tang must be inserted through an aperture well into the extractor. The bottom wall is cut away into a wedge shaped shoulder formation having vertical side shoulders and a horizontal bottom wall. A downwardly directed transverse wall is spaced rearwardly of the aperture.

The blade and holder are inserted into the aperture and then moved downwardly so that the heel of the blade is displaced upwardly by the shoulders. The blade holder is withdrawn rearwardly to cause the then upwardly extending heel portion of the blade to intercept the lower edge of the transverse wall which stops its motion and separates from the tang of the holder.

Eldridge et al. U.S. Pat. No. 4,344,532, shows a surgical blade remover having a plurality of blade holder tang sized slots in a plate. A layer of adhesive material is positioned on the top surface of the plate. A blade is removed by dropping the tang of the blade holder into the slot and then pressing it downwardly so that the blade which projects sidewards beyond the tang is forced off of the tang and adhered to the top surface of the plate. The tangs may then be withdrawn from the slot leaving the blade adhered to the top plate. A raised rib position adjacent to the edge of a slot may be utilized as a pressure point for springing the heel of a blade off of a tang to assist blade removal. Otherwise the top surface of the plate is tapered to provide a deeper recess where the heel of the blade would normally rest allowing a pivoting of the tang of the blade holder away from the blade.

The Grieshaber and Montelius blade removing tools require an intricate manipulation by both hands of the doctor.

The Brimmer et al., Gaskell, Magney and Thompson blade extractors, while capable of being mounted to a surface so that a blade may be removed with one hand operation, require a manipulation of the blade and blade holder to a point where upon a rearward movement of the blade holder tang the blade is pried from the tang of the holder. The operation requires a certain amount of intricate and possibly time consuming manipulation to catch the rear or heel of the blade.

Eldridge, Jr., et al. show a surgical blade remover which is large and cumbersome as it has but a single use for each blade removing slot.

All of the prior art blade removers are complicated structures themselves, each having plural components, plural shoulders and requiring intricate manufacturing, forming and assembly. Such complicated structures with their various faces, shoulders, and crevices and lips are difficult to keep clean.

What is desired is a simple structure which is economical to manufacture and easy to keep clean which can be utilized to extract surgical and scalpel blades from a blade holder tang with a simple operation and without intricate manipulation.

An object of the present invention is to provide simple structure which is usable as a surgical blade removing tool.

Another object of this invention is to provide such a blade removing tool which can be mounted on a fixed surface and which will enable simple single hand operation for removing the surgical blade.

A further object is to provide such a blade removing tool which does not require intricate manipulation for blade removal.

An even further object of this invention is to provide such a blade removing tool which does not require the tang of the blade holder to come in contact with the blade removing tool.

SUMMARY OF THE INVENTION

The objects of this invention are realized in a scalpel blade removing tool for use on a commonly available blade and blade holder. The tool is capable of free standing or of being affixed to a mounting surface so that the blade can be removed from the tang of a blade holder with one hand operation.

An upstanding plate carries a vee shaped slot or notch of sufficient dimensions and specific included angle to bear against the heel of a surgical blade and to wedge in the notch while allowing the narrower tang portion of the blade holder to drop below.

The vee slot permits blade carrying tang to be moved downwardly into the vee until a resistance is felt which lifts the heel of the blade off of the tang which tang then is moved downwardly and rearwardly thereby freeing the blade from the tang. The blade springs forward from the torque imparted on it by the releasing action. The vee is deep enough so that the tang may be pulled out of the notch without touching the side walls thereof.

The vee notch containing upstanding plate may be held in position by a base plate or by being incorporated as a face of a collection box, which collection box may or may not have a closed top.

DESCRIPTION OF THE DRAWINGS

The features, advantages and operation of the invention will be readily understood from a reading of the following detailed description in connection with the accompanying drawings in which like numerals refer to like elements and in which.

DETAILED DESCRIPTION OF THE INVENTION

Figure 1:
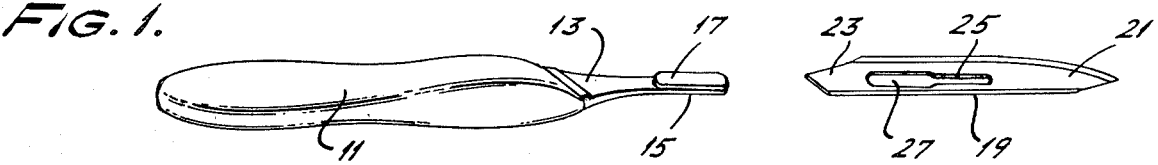
FIG. 1 shows a surgical blade and blade holder commonly known as a scalpel blade in disassembled form.

A surgical blade remover tool is used for removing sugical or scalpel blade inserts from surgical blade holders. A very common type of surgical blade and blade holder is shown in FIG. 1. A broad flat handle portion 11 is contoured for ease of grip and handling. A narrow neck portion 13 extends from the end of the handle 11. This neck portion 13 leads to a single tang 15 having a tapered foot 17 mounted thereon and extending along a portion of the length of the tang 15 from its free end.

The surgical blade 19 includes a knife edge 21 extending from the point to the heel 23 of the blade 19. A slot is formed in the center portion of the blade 19 and has a narrow section 25 at the edge 21 end and a wider section 27 at the heel 23 end. The narrow slot section 25 is of a dimension to fit tightly against the foot 17 on the tang 15. The wider slot section 27 is slightly wider and longer than the foot 17.

The top face of the foot 17 is slightly wider than its base which meets the tang 15. The wide walls of this foot taper from this wider width to the narrower width. This taper is used to wedge the surgical blade 19 tightly on the tang 15.

Figure 2:
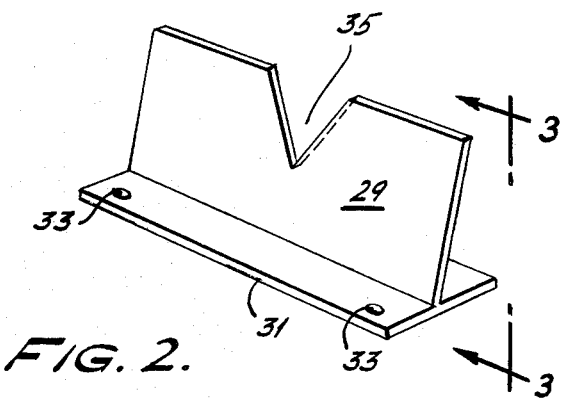
FIG. 2 shows the blade removal tool in its simplest form.

FIG. 2 shows the blade removal tool as an upstanding plate 29 of $\frac{1}{8}$" to 3/32" thick stainless steel plate. The plate 29 is approximately 2½"0 to 3" high and 3 to 3¼ long. It is welded to a base plate 31, of the same material, which is approximately 2" wide and the same length as the upstanding plate 29. A pair of screws 33 extend through the base plate 31 for mounting the base plate to a fixed surface. A vee notch 35 is cut in the top edge of the upstanding plate 29 to extend approximately 1 to 1¾" vertically downwardly from the top edge and to have an included angle of from 30° to 45°. While the included angle, the angle at which the two edge of the notch meet, can vary to less than 30° or more than 45°, for those types of surgical blades 19 and blade holders 11 most commonly found in the marketplace, and includes an angle of about 30° to 35° works well.

Figure 3:
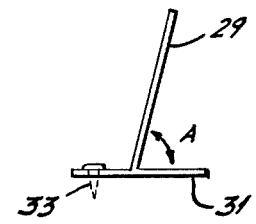
FIG. 3 shows a side view of the embodiment of FIG. 2.

Base plate 31 is welded to the upstanding plate 29 so that the upstanding plate 29 is canted to extend upwardly at an angle "A", which is in the range of about 70° to 85° from horizontal FIG. 3.

Figure 4:
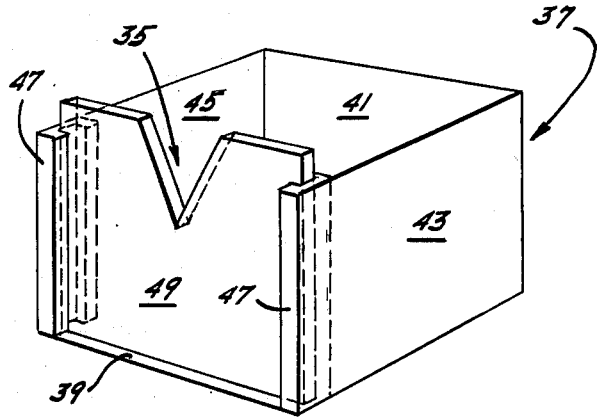
FIG. 4 shows the blade remover vee notch plate held upright and forming one end of a collection box, this collection box having an open top.

It is often desirable to provide a collection box for used surgical blades 19 so that the doctor need not handle a loose blade nor subject himself or others to the hazard of a contaminated blade. FIG. 4 shows a rectangular collection box 37 having a bottom 39 rear 41 and side walls 43,45 respectively. A U-shaped guide 47 extends along the open edge of each of side walls 43,45 from the bottom 39. The collection box 37 is approximately 4¼" long, 3¼" wide and 3¼" high.

A face plate 49, which is approximately 3" wide and 3½" high, is inserted to be held by a pair of U-shaped guide 47 to form the front face 49 of the box 37. This face plate 49 has the same vee notch 35 cut in its top edge and extending downwardly.

The front face 49 has the vee notch 35 extending at the center thereof from its top edge downwardly a distance of approximately 1¾". The opening across the vee notch 35 at the top edge of the face plate 49 is approximately 1" long. The included angle of the vee notch 35 is approximately 33°. The walls of the collection box 37 as well as the face plate 49 bearing the vee notch 35 can all be made of the same material. As an example this material can be 1/16" to 3/16" stainless steel sheet. The U-shaped guides 47 can be made of similar material. Construction can be by standard sheet forming procedures and assemblies, such as welding and stamping.

Figure 5:
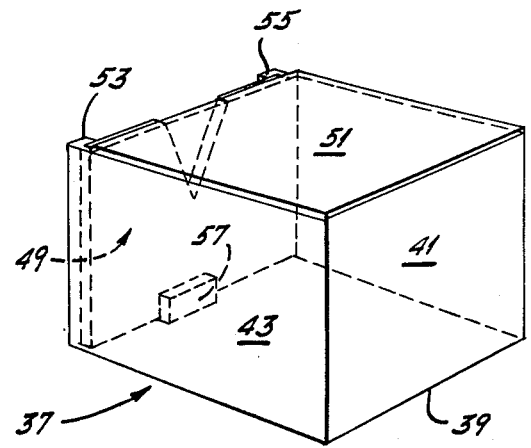
FIG. 5 shows a further embodiment of the invention with the blade removal plate carrying the vee notch held upright and formed as an end wall of a collection box, this collection box having a covered top.

Collection box 37 can have its top closed in with a top plate 51, FIG. 5. In this instance, each of the side walls 43, 45 can have an inwardly turned lip 53, 55 respectively, which extends inwardly along the front face of each side 43, 45. In this embodiment, FIG. 5, the pair of U-shaped guides 47 can be eliminated with the addition of a small rectangular block 57 mounted at the forward edge of the bottom 39.

The face plate 49 is inserted behind the pair of lips 53, 55 and in front of the block 57, to be held securely in position by those members, as well as by the forward edge top plate 51.

Figure 6:
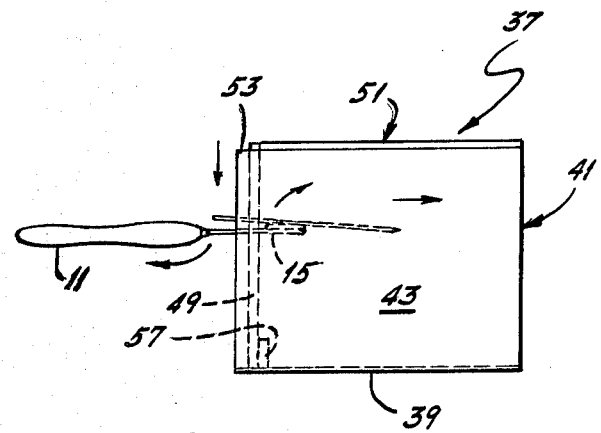
FIG. 6 shows a side view of the blade removal tool of FIG. 5 from a side view showing the removal and collection operation when the blade bearing handle is inserted into the vee and withdrawn.

FIG. 6 shows a side elevation of the closed collection box 37 embodiment of FIG. 5 showing the surgical blade holder 11 with the blade 19 being inserted through the vee notch 35 and moved downwardly. This downward movement wedges the heel of the blade 19 against the converging side walls of the vee notch 35 to exert a force on the heel of the blade 19 enabling the blade 19 to move along the tang 15 to align the larger slot 25, with the foot 17, whereby as the holder 11 is withdrawn out of the box 37 rearwardly and downwardly the foot 17 completes its alignment with the wider slot 25 portion of the blade 19 freeing the blade 19 to spring forward and slightly upwardly into the collection box 37 from the torque asserted on it.

Figure 7:
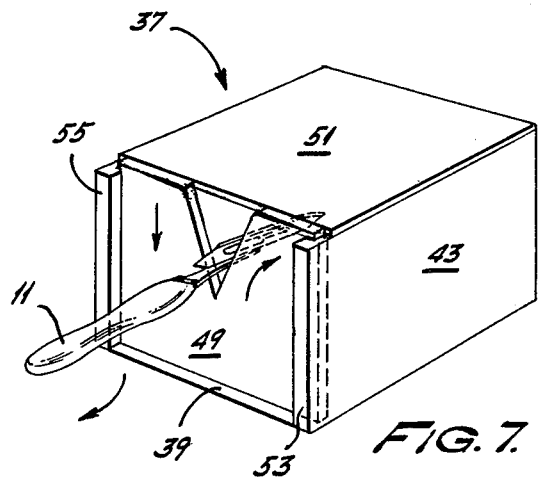
FIG. 7 shows the removal operation with the apparatus of FIG. 6 from a different perspective view.

FIG. 7 shows the blade removal operation of FIG. 6 from a front perspective view.

An alternate structure embodying the invention can include any plate having a vee-shaped notch in it and being associated with any of a plurality of containers. As an example it is possible to use a commercially available glass or plastic jar with a screw on type metal lid, or a fiber or reinforced plastic lid. The lid would contain the vee-shaped opening.

Changes may be made in the above described invention without departing from the intent, scope or method of operation thereof. It is intended, therefore, that the above description be read in the illustrative sense and not be interpreted as limiting the invention.

What is claimed is:

1. A surgical plate remover for separating a surgical blade from a blade holder with spring action comprising:
   a plate;
   means for holding said plate in a relatively secured position; and
   a vee-shaped notch in an essentially flat section of said plate, said notch being to engage the sides of said blade at the heel portion thereof when said blade is inserted partially therethrough for springing said blade off of said holder.

2. The blade remover of claim 1 wherein said plate is an upstanding plate; and wherein said vee-shaped notch is in said upstanding plate.

3. The blade remover of claim 1 wherein said vee-shaped notch extends from the top edge of said upstanding plate downwardly.

4. The blade remover of claim 2 wherein said vee-shaped notch has an included angle of about from 3° to 45°.

5. The blade remover of claim 3 wherein said vee-shaped notch is approximately 1¾" deep.

6. The blade remover of claim 4 wherein said vee-shaped notch has an included angle of approximately 33°.

7. The blade remover of claim 1 wherein said upstanding plate holding means is a base plate welded to said upstanding plate.

8. The blade remover of claim 6 wherein said base plate and upstanding plate are welded with an included angle of 70° to 85°.

9. The blade remover of claim 1 wherein said upstanding plate holding means includes a collection box having:
   a bottom side;
   a rear face;
   a right and left sides; and
   U-shaped guides extending vertically one each along the front end of each of said right and left sides on the inside thereof, parallel and facing one another;
   wherein said upstanding plate is held vertically by said U-shaped guides as the front face of said box.

10. The blade remover of claim 1 wherein said upstanding plate holding means includes a collection box having:
    a bottom side;
    a rear face;
    a right and left sides;
    an inwardly projecting lip extending vertically along the front edge of each of said right and left sides;
    a top plate being slightly shorter than said bottom side and leaving a space at the front of said box; and
    a bumper block on the inner face of said bottom side near said front and slightly positioned therefrom;
    wherein said upstanding plate is held vertically in position as the front face of said box by nesting against said pair of lips, said block and said top plate.

11. A method of separating a surgical blade from a blade holder, said blade having a center longitudinal slot engaging a foot mounted on a tang projecting from said holder handle, wherein the heel portion of said blade extends beyond the sides of the tang and foot, comprising the steps of:
    establishing a vee-shaped notch in a plate;

inserting said blade and holder partially into said notch to wedge the sides said heel portion of said blade against the converging sides of said notch;

drawing said handle and tang further into said notch toward the vertex thereof to create a torque on said blade emanating from said heel portion; and pulling said handle and tang rearwardly out of said notch freeing said blade from said tang to cause said blade to spring forward off of said tang and out of said notch under said torque created on said blade.

12. The method of claim 11 wherein said blade longitudinal slot has a narrow portion contiguous with a wider portion, said wider portion being near said heel of said blade; wherein said step of rearward pulling of said handle and tang causes said blade slot wider portion to slide adjacent said tang thereby freeing said blade from said tang and permitting said spring forward movement.

* * * * *

UNITED STATES PATENT AND TRADEMARK OFFICE
CERTIFICATE OF CORRECTION

PATENT NO. : 4,466,539

DATED : August 21, 1984

INVENTOR(S) : Surgical Blade Remover

It is certified that error appears in the above-identified patent and that said Letters Patent is hereby corrected as shown below:

Col. 6, line 4,     "plate" should be -- blade - -.

Col. 6, line 22,     "3°" should be - - 30° - -.

Signed and Sealed this

Eighth Day of January 1985

[SEAL]

Attest:

GERALD J. MOSSINGHOFF

*Attesting Officer*

*Commissioner of Patents and Trademarks*